United States Patent
Pagano et al.

(10) Patent No.: US 7,555,954 B2
(45) Date of Patent: Jul. 7, 2009

(54) IN-TRACK WHEEL INSPECTION SYSTEM

(75) Inventors: Dominick A. Pagano, Weston, CT (US); David W. Giragosian, Waterbury, CT (US)

(73) Assignee: Dapco Industries, Inc., Ridgefield, CT (US)

( * ) Notice: Subject to any disclaimer, the term of this patent is extended or adjusted under 35 U.S.C. 154(b) by 204 days.

(21) Appl. No.: 11/412,318

(22) Filed: Apr. 26, 2006

(65) Prior Publication Data

US 2006/0266122 A1    Nov. 30, 2006

Related U.S. Application Data

(60) Provisional application No. 60/675,019, filed on Apr. 26, 2005.

(51) Int. Cl.
*G01N 29/04* (2006.01)

(52) U.S. Cl. .......................... 73/620; 73/634

(58) Field of Classification Search .................. 73/598, 73/620, 634, 636
See application file for complete search history.

(56) References Cited

U.S. PATENT DOCUMENTS

| | | | |
|---|---|---|---|
| 3,812,708 A | | 5/1974 | Cowan et al. |
| 5,349,861 A | * | 9/1994 | Catot et al. ................... 73/598 |
| 5,777,891 A | | 7/1998 | Pagano et al. |
| 5,864,065 A | * | 1/1999 | Prorok et al. ................. 73/622 |
| 6,401,044 B1 | * | 6/2002 | Ibanez Rodriguez et al. .. 702/39 |
| 6,862,936 B2 | | 3/2005 | Kenderian et al. |

* cited by examiner

*Primary Examiner*—John E Chapman
(74) *Attorney, Agent, or Firm*—Keith D. Nowak; Carter, Ledyard & Milburn LLP

(57) ABSTRACT

An ultrasonic real-time inspection method which is user-friendly in an interactive environment to provide ease of operation, as well as a combination of consistency, thoroughness, and speed of operation in flaw detection not achievable by other methods. The system and method are useable on a traveling wheel so as not to unduly interfere with normal train operation. The system and method includes a test device that moves along train wheels injecting pulses into the wheel to detect acoustic responses caused at a discontinuity in the wheel. A processor can also be included to determine a pattern of a feature of the wheel associated with the discontinuity.

9 Claims, 14 Drawing Sheets

Plan View

Plan View at Drive Rack

Side Elevation

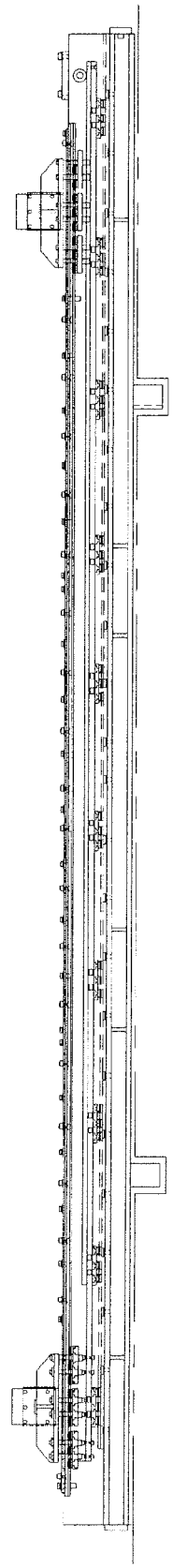
Section at Drive Rack
FIG. 7f
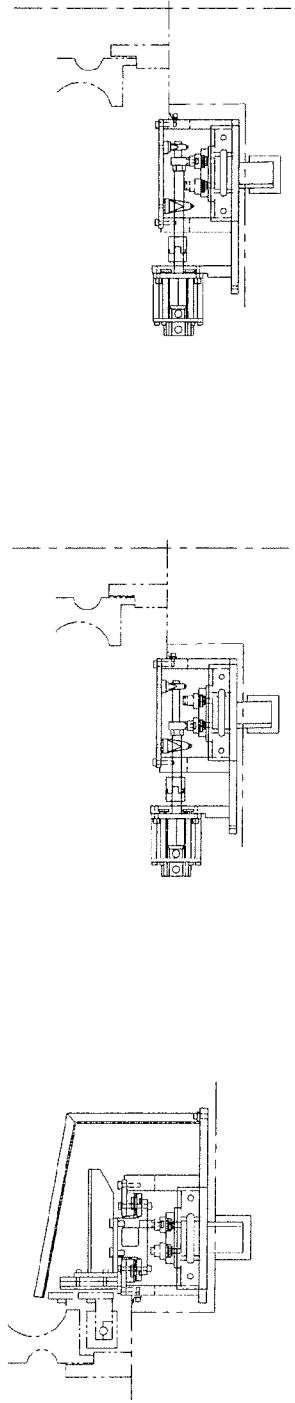
FIG. 7h
FIG. 7i
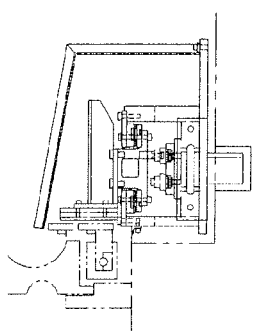
FIG. 7g Side Elevation Showing Powertrack

FIG. 10

IN-TRACK WHEEL INSPECTION SYSTEM

CROSS-REFERENCE TO RELATED APPLICATIONS

This application claims priority to U.S. provisional patent application Ser. No. 60/675,019, filed Apr. 26, 2005, entitled "IN-TRACK WHEEL INSPECTION SYSTEM," which is hereby incorporated by reference in its entirety. Related Applications application Ser. No. 10/652,279, filed Aug. 28, 2003, now issued U.S. Pat. No. 7,054,762, which claims priority to U.S. provisional patent application Ser. No. 60/406,842, both entitled "METHOD AND SYSTEM FOR ANALYSIS OF ULTRASONIC REFLECTIONS IN REAL TIME", filed Aug. 29, 2002, are also all incorporated herein by reference in their entirety.

FIELD OF THE INVENTION

This invention relates to real time ultrasonic non-destructive testing systems and methods. More particularly, this invention relates to systems and methods that offer advances in real time ultrasonic flaw detection in railroad wheels.

BACKGROUND OF THE INVENTION

Railroad maintenance is one of the greatest problems facing the transportation industry today. It is estimated that annual costs related to cracked railroad wheels is at least $24 million. This problem of cracked railroad wheels continues to grow. Estimates are that there at least 5% more cracks per year while other sources estimate that there may be 12% to 15% more faults with respect to railroad wheels per year.

There are several types of defects with respect to railroad wheels, the primary ones being, thermal cracks, vertical split rim and shattered rim cracks. Thermal cracks, which include tread and flange tip cracks, account for approximately 8,000 to 10,000 wheel replacements every year. Shattered rim cracks account for another 300 to 500 wheel replacements per year.

As shown in FIG. 1, thermal cracks 6 occur on the tread 12 and flange 2 of a typical wheel. Additionally, a shattered rims 8 and vertical split 10 can be seen in FIG. 1.

It should be noted that other than by visual inspection, no technique is readily available today to perform inspections on railroad wheels while they are still mounted on trains. Prior acoustic inspection techniques have proven to be unreliable and generally limited to surface thermal crack detection, as described in the U.S. Pat. No. 3,812,708, Most conventional testing systems use a contact system whereas the laser air hybrid ultrasonic technique (LAHUT) system as described in U.S. Pat. No. 6,862,936 is a non-contact system.

What is needed is a robust system that can reliably detect flaws in railroad wheels while the train is in operation.

SUMMARY OF THE INVENTION

Efforts have been focused on developing a wayside, automated ultrasonic inspection system capable of detecting cracks in railroad wheels that are inspected under a moving train. Disclosed is a system and method for in-track wheel inspection. The system utilizes ultrasonic inspection and or visual inspection.

The system preferably detects defects in wheels at speeds of approximately 5 to 8 miles per hour. In one embodiment, the system can test wheels, both above and below the given speed range. Additionally, while rail wheels of 28" to 42" can be tested, wheels outside this range, if used, can be analyzed using the same system. The system is optimized to detect shattered rim defects of 0.5" diameter or less but larger rim defects can be detected. Tread thermal fatigue cracks of at least 0.5" in length and 0.031" deep or larger are the optimal fatigue crack detection sizes. However, smaller thermal fatigue cracks can be detected. Finally, flange thermal cracks smaller than 0.25" long and 0.062" can be detected.

One embodiment of the system is designed to preferably test a wheel in four quadrants as shown in FIG. 2. In one embodiment, one third wheel segments can be tested. Because of the size of a wheel and the configuration of the wheels on a truck of a car in a train formation, it is impractical to test a wheel in one half wheel segments, although it can be done. A wheel can be tested in one third wheel segments or, if desired, smaller segments can be used such as eight segments. When the wheels are analyzed, there is preferably an overlap of approximately 10%. Further, in another embodiment, the quadrants are tested in different orders, i.e., first quadrant, third quadrant, second quadrant, and fourth quadrant. This is done so as to allow the adequate cycle time for the transducer arrays to engage the rolling wheel, inspect its designated quadrant, and return to home position to allow the process to start on the next wheel to enter the test array. Likewise, four separate testing stations are used in one embodiment, one for each wheel.

In another embodiment, an entire wheel is tested. In the preferred embodiment, four separate testing stations test one complete wheel of a four wheel sequence. Test heads travel through three zones, an acceleration zone, a data collection zone, and a deceleration return to home position zone. In one embodiment, in a four wheel sequence, the order of testing will be a synchronous and based on train speed and formation, but the first test station will always test the first wheel of a four wheel sequence as will the second test station will test the second wheel, third station third wheel, and then finally, the fourth station the fourth wheel. So sequentially the first station will inspect the first wheel, fifth wheel, ninth wheel, thirteenth and so on.

DESCRIPTION OF THE FIGURES

FIG. 7a-7k are a set of drawings detailing one embodiment of the invention;

FIG. 10 depicts an output screen according to the present invention.

DETAILED DESCRIPTION OF THE PREFERRED EMBODIMENT

The present invention discloses a system and method for in-track wheel inspection. The system can be used to perform real-time defect recognition on a train wheel by detecting the train wheel entering a test station, accelerating a test head to match the speed of the train wheel, injecting, from the test head, pulses of a plurality of ultrasonic beams into the train wheel, detecting acoustic responses caused at a discontinuity of the elongated material, determining at least one characteristic of the detected acoustic responses, for example a beam pulse speed and determining a pattern of a feature of the wheel associated with said discontinuity based on the at least one characteristic and at least one pattern recognition rule. A pattern of a feature of the wheel is determined by classifying features associated with the responses, clustering the classified features, performing basic recognition analysis using theclustered classified features to determine a basic recognition and performing context recognition analysis on the basic recognition to determine the pattern.

Figure 1:
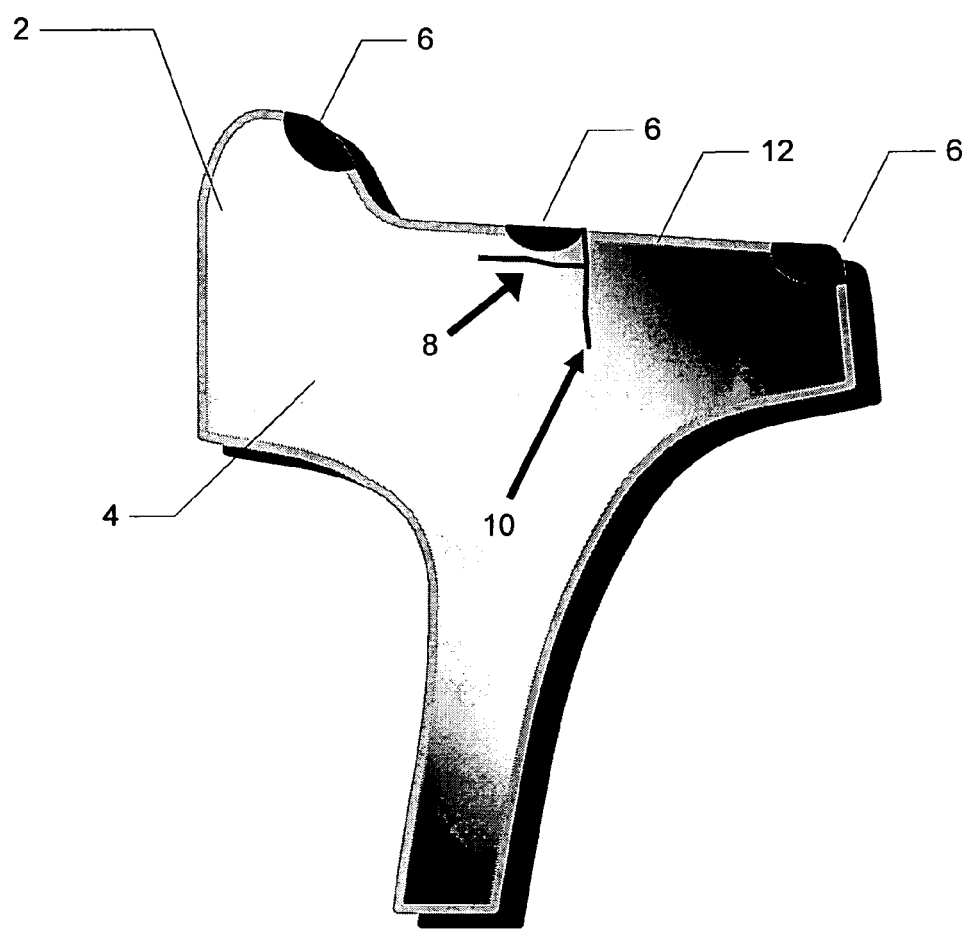
FIG. 1 depicts a cross section of a defective railroad wheel.

FIG. 1 shows a cross-section of a standard railroad wheel. The wheel shows the various defects that typically develop over time during the use of the wheel. The defects include thermal cracks on the tread and flange of the wheel 6, such as vertical split 10 and defects such as shatters or cracks in rim 8. The disclosed apparatus provides a system and method for detecting wheel defects for a moving train. The disclosed system preferably utilizes ultrasonic defect detection.

Ultrasonic non-destructive wheel testing involves the use of ultrasonics to test the steel of a wheel, without damaging the wheel in the test process. This technique relies on the ability of the ultrasonic vibrations to propagate through the material, and to blocked or reflected off discontinuities such as voids or cracks in the material. Ultrasonics is the use of sound waves which have a frequency which is higher than an adult human is able to hear (greater than 20,000 cycles per second). In many ways, ultrasonic testing is similar to the use of radar or sonar, in that reflections of the sound energy can be used to detect or identify targets or "features." Just as a light beam will reflect off a wall, a beam of sound energy will reflect off a discontinuity in the medium (e.g., the material, the steel of the rail). In some instances, the reflection will be a normal wheel feature, such as the hub or axle. In such cases, the feature is considered "normal" and the reflection is not reported as an anomalous condition. The skill in ultrasonic testing lies in discriminating between normal features, and abnormal conditions, such as voids or cracks in the rail structure.

Figure 2:
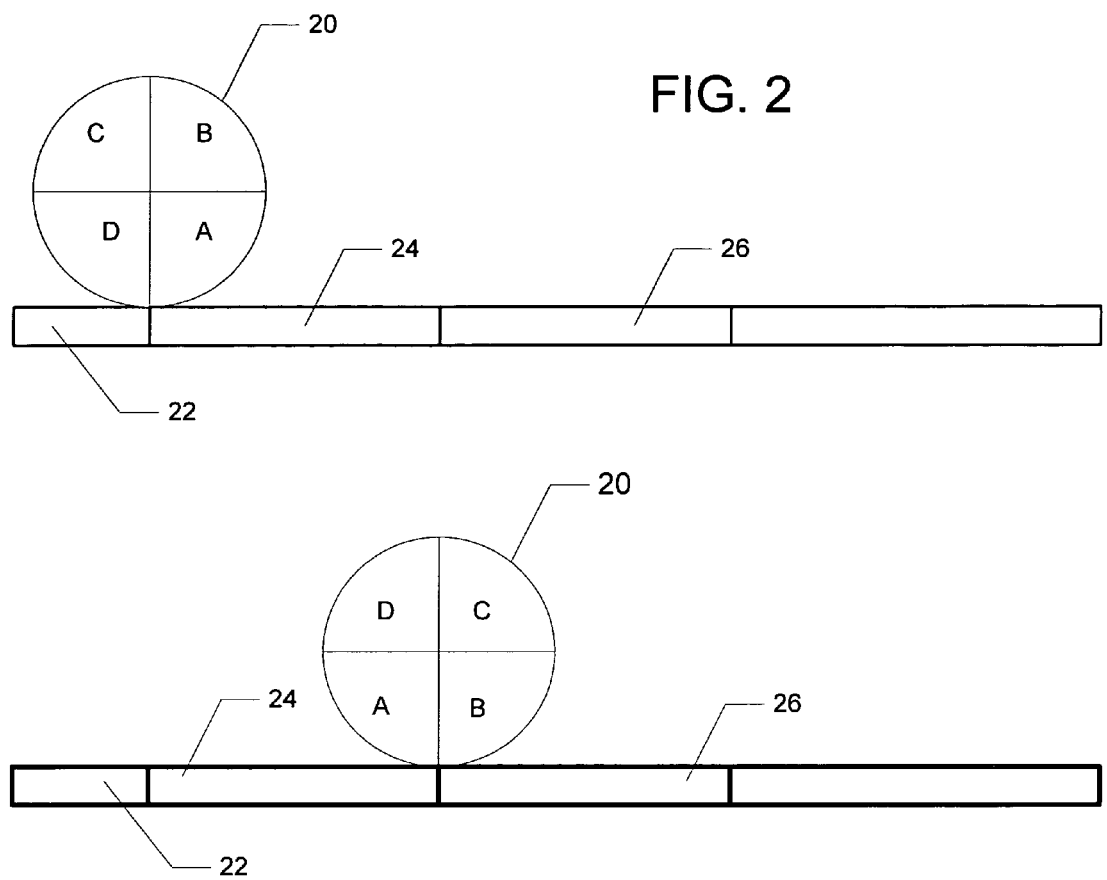
FIG. 2 depicts a test setup according to one embodiment of the present invention.

In a first embodiment of the invention, as shown in FIG. 2, a wheel 20 is preferably divided into four quadrants, A, B, C, and D. The wheel 20 rides on track 22. During operation, the first quadrant of wheel 20, quadrant A, rolls over first testing station 24. While the wheel passes over station 24, it is subjected to test signals. In a preferred embodiment, the test signals are ultrasound signals. The ultrasound signals are then detected using laser and/or ultrasound detectors.

In a preferred embodiment, the wheel passes the system at speeds of approximately 5-8 miles per hour. However, it should be noted that slower or faster speeds could be used during the testing process. Additionally, the system is designed for use with standard rail car wheels ranging in diameter from 28 inches to 42 inches. However, smaller or larger wheels can be tested with the disclosed system.

In one embodiment, the testing areas 24 and 26 each test one quarter of the wheel. In operation, two additional testing areas would be present to test remaining quadrants C and D. In one embodiment, as the first quadrant of wheel 20 passes over testing area 24, the wheel is subjected to ultrasonic pulsed waves. These emissions are detected using a transducers configured in various transmit/receive modes. In a preferred embodiment, ultrasonic transducers detect the ultrasonic anomalies and used to detect wheel flaws. In a preferred embodiment, the ultrasonic pulses are coupled to the wheel using water or thin film of water.

As the wheel progresses through the testing station, quadrant B is presented to test area 26. Test station 26 is similar to test station 24 in that it subjects quadrant B of wheel 22 ultrasonics and/or laser emissions. It should be noted that in one embodiment, test stations 24, 26, and the like are adapted to test more or less than one quarter of a wheel. In one embodiment, because wheels differ in diameter each test section is programmed to test a select portion of a given wheel.

In a preferred embodiment, the ultrasound energy is coupled to the surface of the rail wheel using a fine water mist. Preferably, distance based pulsing every 1/16 of an inch supplies the ultrasound energy to the wheel. A first set of ultrasound detectors are used to detect the ultrasound pulses in a shear wave move. The shear wave mode detectors detect tread cracks. A longitudinal array of sensors is used to detect shatter rim cracks a third set of transducers are used to detect vertical split rim. A fourth set of transducers are used in a low frequency surface wave mode for the detection of flange cracks. In a preferred embodiment, the low frequency surface wave is approximately 400 kHz.

Figure 3:
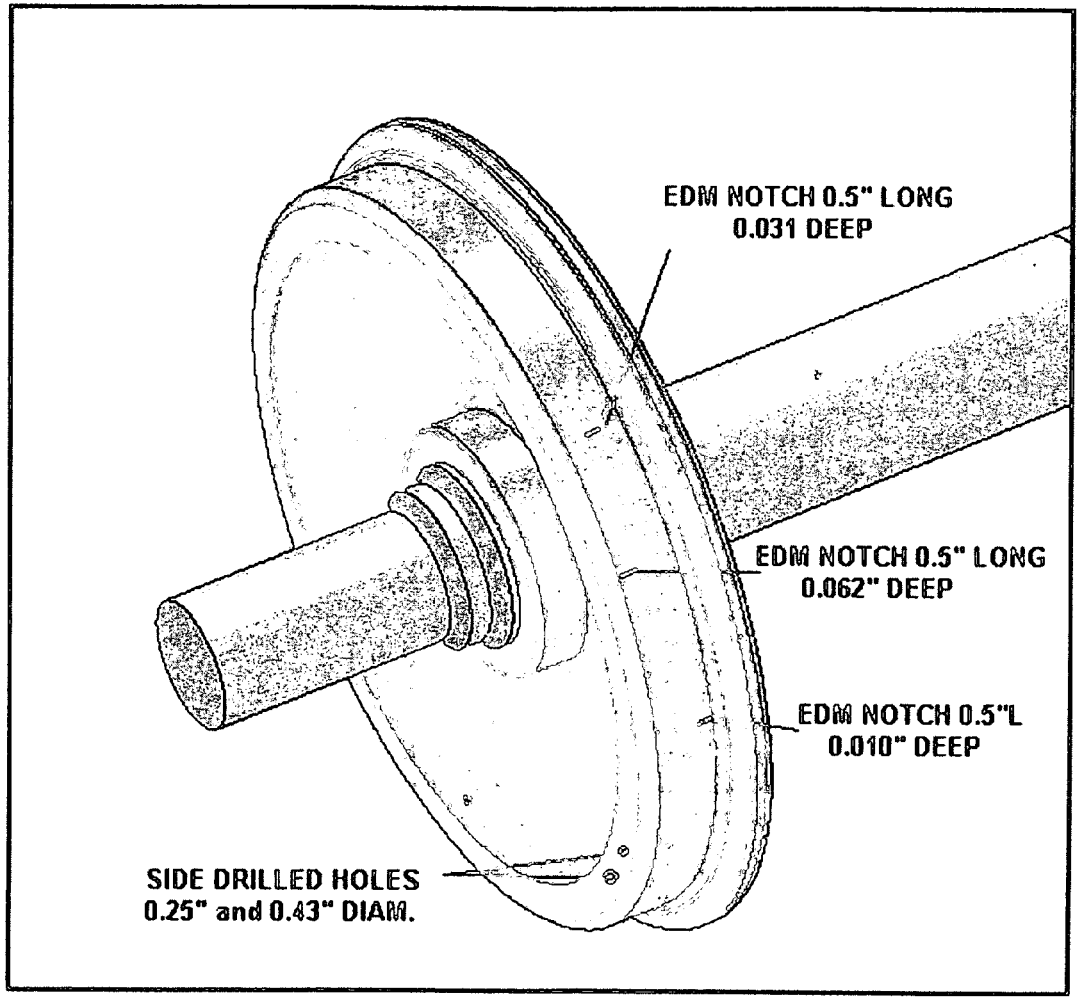
FIG. 3 depicts a calibration wheel.

Since Ultrasonics is a relative science, various EDM (electric discharge machining) notches on a calibration wheel are used. A preferred set of calibration holes and/or notches 15 is shown in FIG. 3. The calibration notches and holes are used to calibrate and verify the system's operation. Because ultrasound transmission to a wheel will vary depending on various surface and environmental conditions including grease, or oil on the wheel surface, rust, and the like, the calibration wheel is used for system static and dynamic calibration to verify actual system 20 conditions prior to test. In another embodiment, the system is self calibrating based on detected results.

In a preferred embodiment, the calibration wheel has a series of notches on the tread 12 such as a ½ inch long 0.0031 inch deep notch, a ½ inch long 0.062 inch deep notch, and a ½ inch by 0.01 inch deep notch. These notches simulate tread cracks. Further, in a preferred embodiment, the calibration wheel includes side drill holes. The side drill holes simulate rim cracks.

Figure 4:
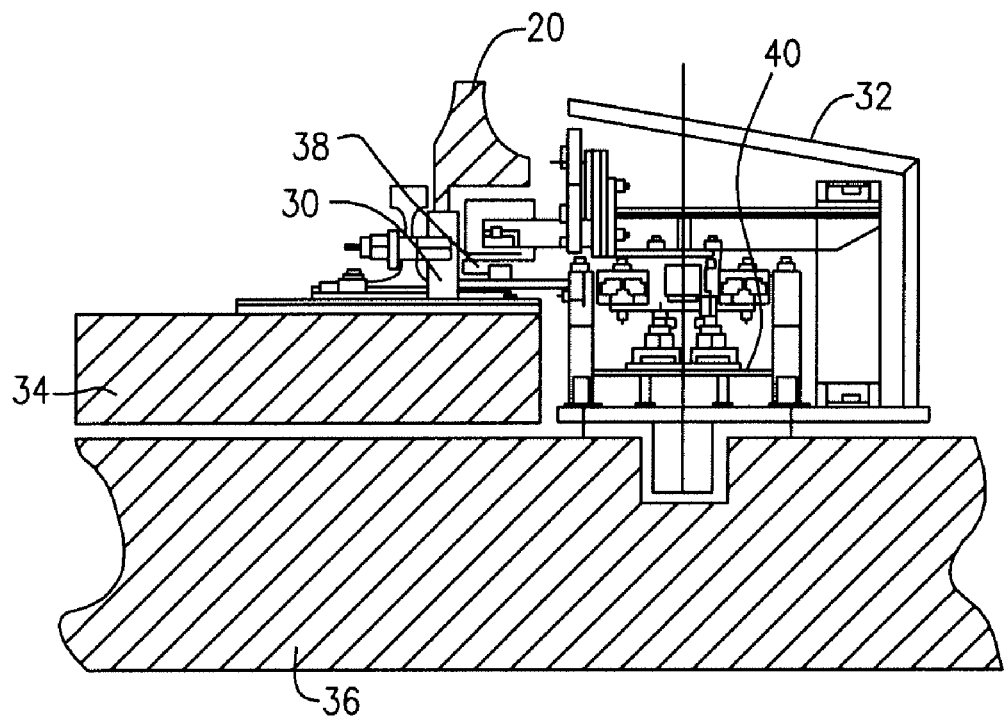
FIG. 4 depicts an end view of one embodiment of the invention.

In a preferred embodiment, as shown in FIG. 4, the railroad wheel 20 rides on a flange bearing track 30. The flange bearing track is designed such that the wheel 20 rides only on the flange thereby exposing the tread surface 12. The running surface or tread 12 of the wheel 20 is then inspected using ultrasonics transducer arrays, electronic data processing and/or pattern recognition to further identify actual defects from anomalies.

In a preferred embodiment, housing 32 protects the testing equipment from the elements. Provided in enclosure 32, are the wheel tracking and testing equipment. The tracking equipment enables the system to move test head 38 in substantial unison with the wheel 20 during test. In a first embodiment, the flange bearing track is mounted to a wooden tie 34. In another embodiment, concrete ties or foundations are used. The tie 34 and testing assembly are then mounted to a foundation 36.

Figure 5:
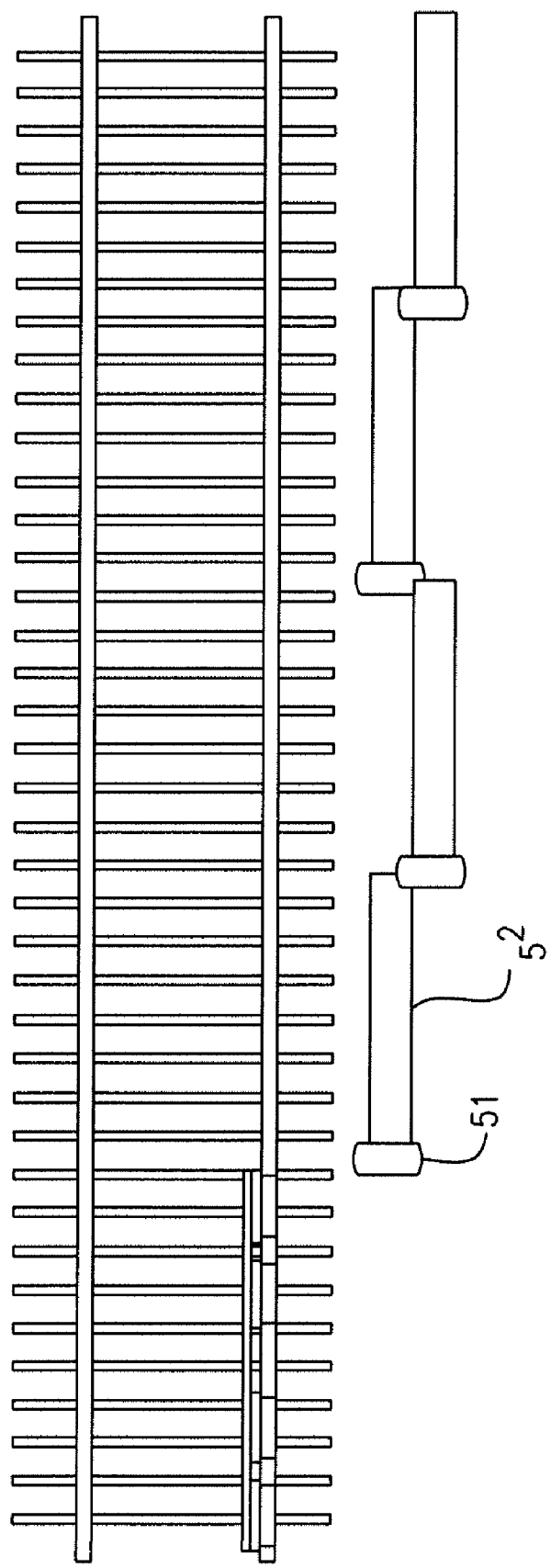
FIG. 5 depicts a test setup according to another embodiment of the present invention.

As shown in FIG. 5, there are four separate testing stations. In this embodiment, each of the testing stations tests a single wheel. In a preferred embodiment, each of the testing assemblies is coupled to a test track approximately 195 inches long. In operation, as a wheel passes its designated test station, the test head tracks the wheel to detect any wheel defects. This manner, a single head tests a single wheel. Further, it should be noted that during tests, the speed of the train is preferably between 5 and 8 miles per hour. However, higher or lower speeds can be used during the testing and defect detection process.

Figure 6:
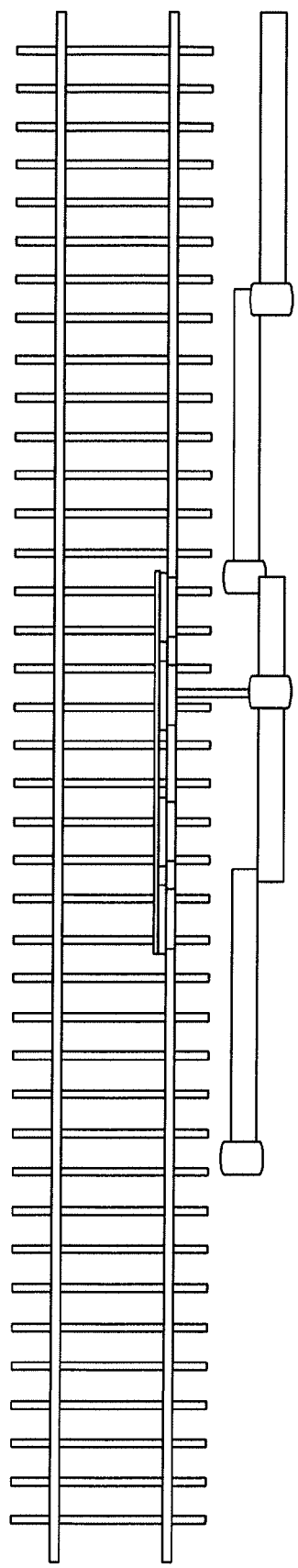
FIG. 6 depicts the test setup of FIG. 5 during a test.
Figure 7A:
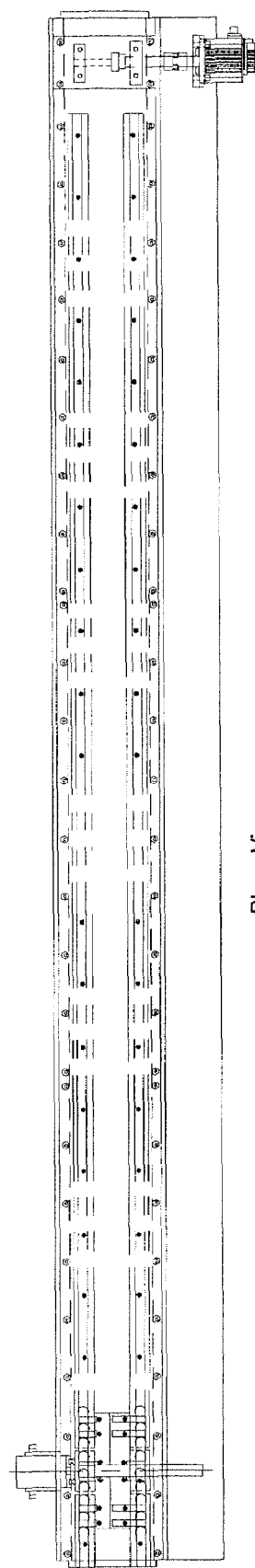
Figure 7B:
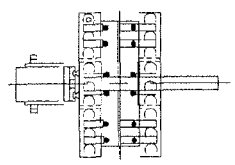
Figure 7C:
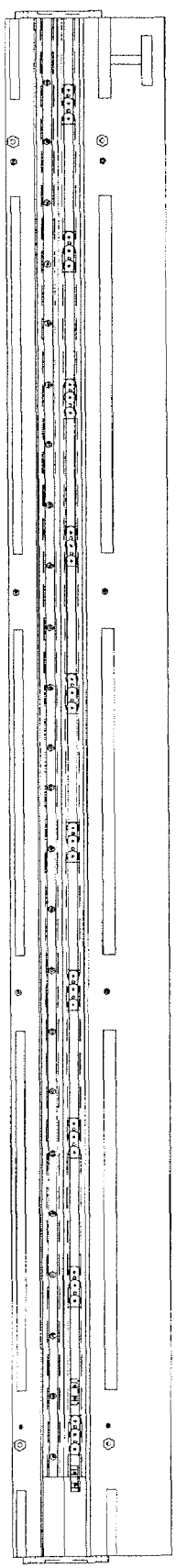
Figure 7D:
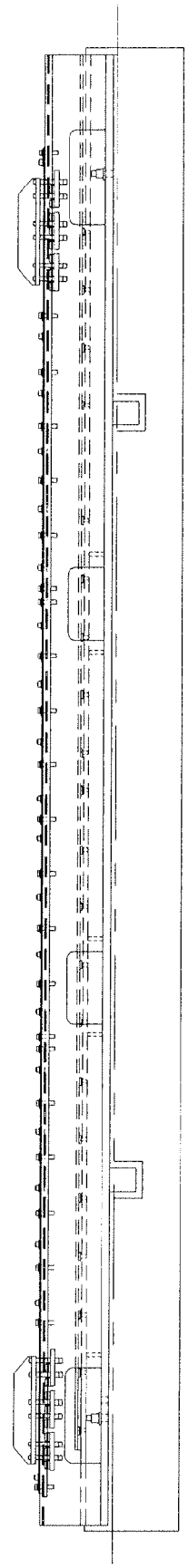
Figure 7E:
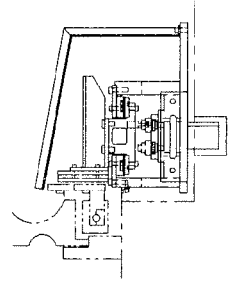
Figure 7J:
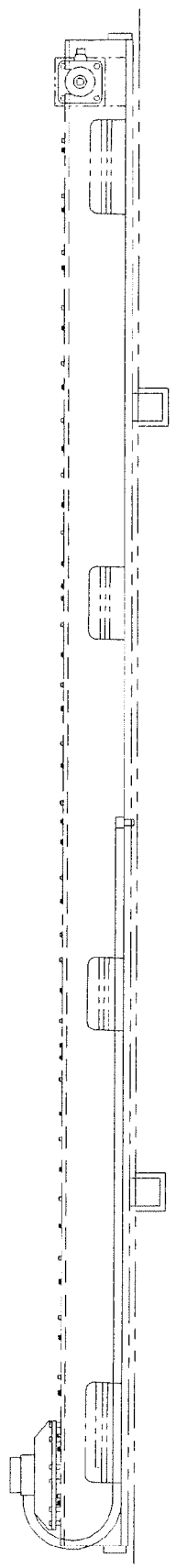
Figure 7K:
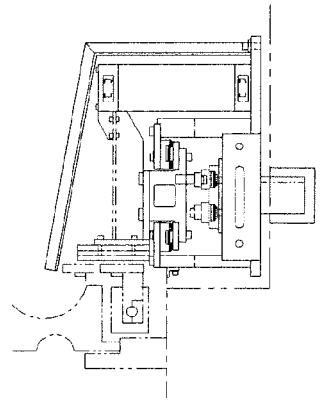

As shown in FIG. 6, the test head of the second test station is testing the second wheel of the four wheel sequence. As the wheel passes the test station, the test head tracks the wheel and engages the ultrasonic sensors and determines if the wheel has flaws. Once the data collection is completed, the head returns to home position awaiting the second wheel of the next four wheel sequence.

In operation, as the first wheel reaches the first detection station, the test head locks onto the wheel and travels in a direction of the wheel from a first end 51 to a second end 52. Although not shown, the track in FIG. 5 is the flange bearing track shown in FIG. 4. The test head travels beneath the wheel and tests one entire wheel. In this manner, each of the four testing stations tests one of the four wheels on a standard train truck. It should be noted that other configurations are possible where only portions of a wheel are tested at each testing station.

FIG. 7 shows the detail of the test section of the track. As shown, there is a test track upon which the test head rides that is parallel to the flange bearing track upon which the wheel 20 rides. The parallel track allows the testing apparatus to travel under the running surface of the wheel 20 and examine that surface. It should be noted that in this embodiment, because four separate testing stations are utilized; one station tests an entire wheel. Once a test station completes testing a wheel, it resets so that it is ready for the next wheel it is designated to test. Having the tracks mounted next to one another provides the special relationship to test the wheel as it passes the testing station. The dynamic nature of the test provides for in-situ testing of a train without the need to remove a train or individual cars from service so as to test its wheels.

Figure 8:
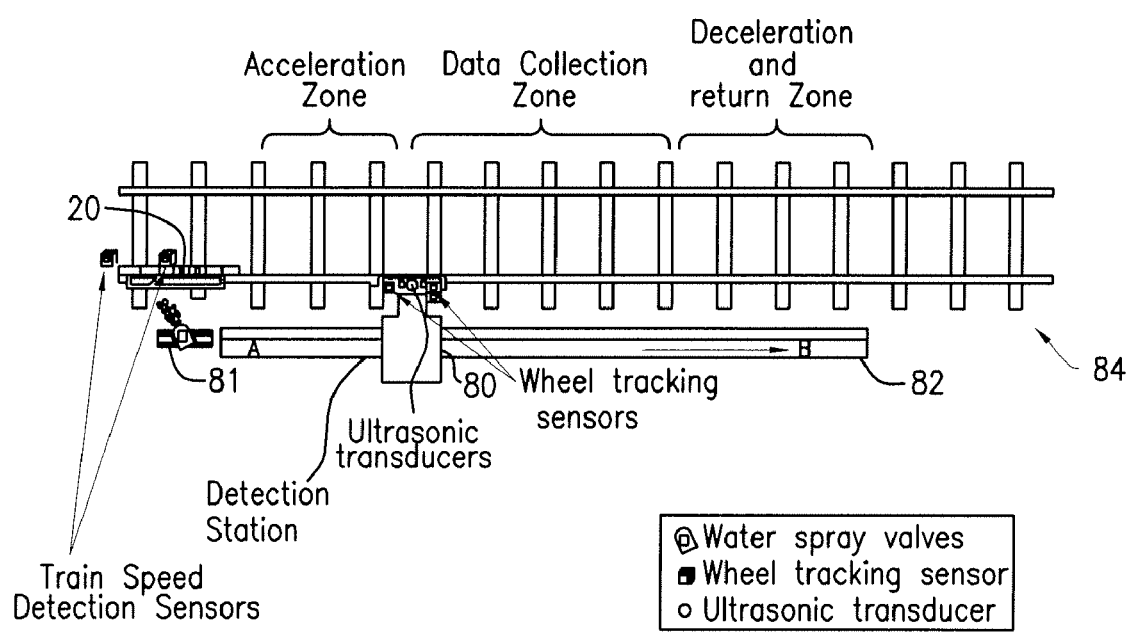
FIG. 8 depicts another embodiment of the invention.

FIG. 8 shows another embodiment of the invention. As shown in FIG. 8, ultrasonics are used. As shown, a wheel approaches a first area water vapor 81 is sprayed onto the wheel 20 to be tested. The water vapor 81 aids in coupling the ultrasonic emissions to the wheel. A dynamic detection station 80 rides on track 82 which parallels flange bearing track 84. When the wheel reaches the beginning (A) of the test head track 82, the test head carriage begins to move alongside the wheel 20 under test. The first area is the acceleration zone where the test head matches the speed with the wheel 20. Next, the test head aligns itself with the wheel 20 to accurately collect data. Finally, a third data collection zone is entered where the test head collects relevant data with respect to wheel defects. After data collection, the test head decelerates and returns to the home position (A).

It should be noted that the system shown in FIG. 8 could be adapted to use only ultrasonics and not include laser testing. In a preferred embodiment, after the testing is performed, if a defect is detected, the defective wheel will be identified by its location in a train. It can also be marked with paint, ink, an electronic tag, or the like. In another embodiment, a report is generated detailing the test results for each tested wheel.

Figure 9:
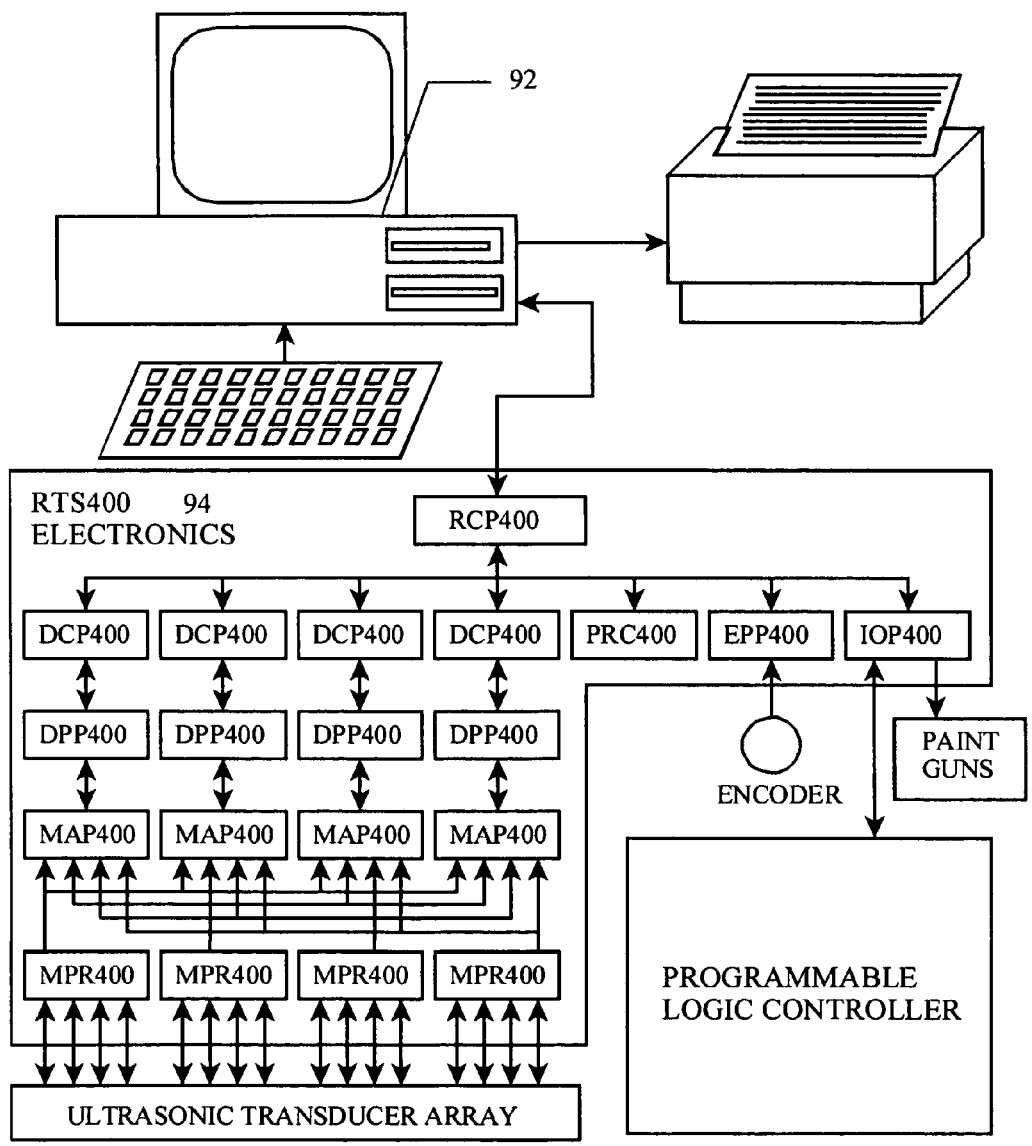
FIG. 9 depicts the computer system used in the system.

FIG. 9 is a test set up for detecting wheel defects. In a preferred embodiment, as shown, an ultrasonic transducer array and associated signal processing is controlled via a computer. It should be noted that the control computer 92 can be at an offsite location different than the testing electronics 94. Additionally, in one embodiment, the ultrasonic transducer array is at a location separate and apart from the electronics and the control computer 92.

The system's unique parallel/multiplexed architecture supports a multiplicity of channel configurations. In one embodiment, sixteen transducers are fully multiplexed into one data processing channel or four of the transducers are parallel fired using four data processing channels with up to four transducers multiplexed into each data channel (e.g. four by four organizations). In all configurations, all transducer channels are user programmable for operations in either thickness measurement or flaw detection.

Flaw detection modes are preferably set for either single or dual sensitivity operating modes. Thickness measurements are processed on every transducer test cycle for all pulse densities. AScan signals are monitored for system setup either on a standard analog or digital oscilloscope, or using a digitizing card located within the operator interface PC.

The operator interface is preferably a menu/dialog-driven, easy to use format with all controls set via the PC's keyboard and mouse. All test parameters for all transducer channels are operator selectable, and all are user level protected using operator access codes. The number of parameter setups which can be saved to disk files for easy recall is limited only by the available disk space.

In a preferred embodiment, the system architecture uses high-speed digital electronics and multiple microprocessors to form the most flexible, highest performance ultrasonic signal processing instrument available for general NDT applications. The instrumentation is provided as a complete turn-key system including the host PC computer for user I/O.

The front-end pulser/receiver electronics consists of four internal plug-in boards, each of which can multiplex up to four transducers. Depending on the application, one to four data processing channels are used to analyze and characterize the ultrasonic data sets received from the pulser/receivers. In a preferred embodiment, scan rates ranging from 100 to 1000 surface feet per minute (33 to 330 meters per minute) are achievable, depending on the mixture of thickness and flaw detection channels defined in the system setup. In other embodiments, higher and lower scan rates are achievable.

Each transducer has two independent gain control settings, one from the excitation pulse to the surface interface signal, and one from the interface signal to the next excitation pulse. This dual gain feature provides enhanced near-surface resolution. The data collection electronics uses two hardware gates during which up to 256 time-of-flight measurements are stored into a FIFO for later data processing. Thousands of software gates can be established within both of the hardware gates as part of the analysis of the ultrasonic data sets by the microprocessor on each data channel.

Figure 10:
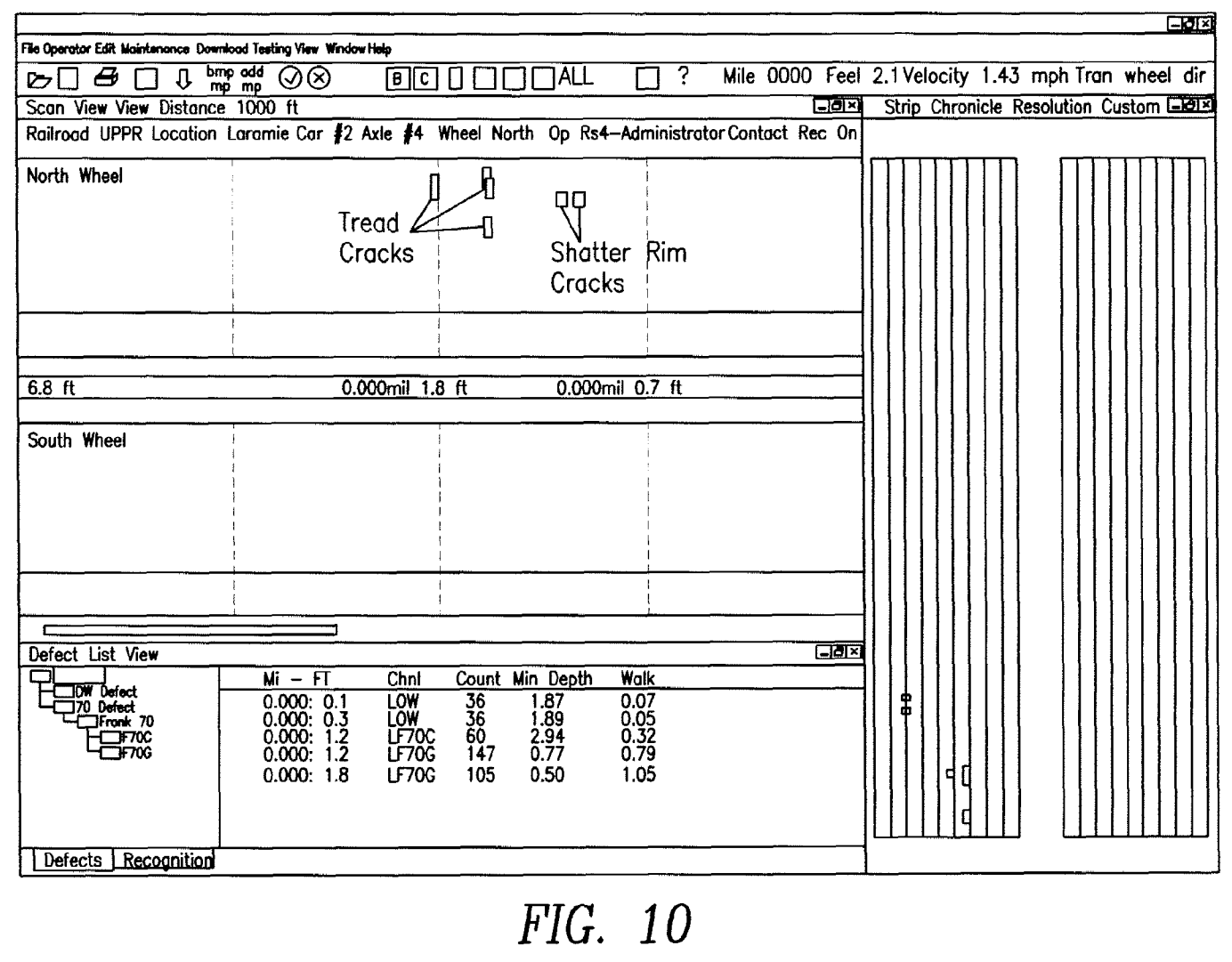

FIG. 10 shows the data used by the system to determine if a crack is present. As shown in FIG. 10, after testing begins at approximately 175 microseconds, the output is fairly smooth indicating that there are no defects in the wheel under test.

FIG. 10 shows a typical display screen for a train wheel under test. As shown, the wheel under test has shattered rim cracks and tread cracks on the north wheel while the south wheel has no defects. The data can be presented in one of a variety of ways either as defect indicators, as numeric output, or as a histogram.

It should be noted that using the present system, ultrasound detection is performed at the wheel rim and tread. Further, each wheel that passes the test station is 100% inspected. Thus, the present system will detect defective wheels and mark those wheels for replacement.

The present invention may be described herein in terms of functional block components, optional selections and various processing steps. It should be appreciated that such functional blocks may be realized by any number of hardware and/or software components configured to perform the specified functions. For example, the present invention may employ various integrated circuit components, e.g., memory elements, processing elements, logic elements, look-up tables, and the like, which may carry out a variety of functions under the control of one or more microprocessors or other control devices.

Similarly, the software elements of the present invention may be implemented with any programming or scripting language such as C, C++, C#, Java, COBOL, assembler, PERL, or the like, with the various algorithms being implemented with any combination of data structures, objects, processes, routines or other programming elements.

Further, it should be noted that the present invention may employ any number of conventional techniques for data transmission, signaling, data processing, network control, and the like. Pattern recognition techniques as described in U.S. Pat. No. 5,777,891 can also be employed.

It should be appreciated that the particular implementations shown and described herein are illustrative of the invention and its best mode and are not intended to otherwise limit the scope of the present invention in any way. Indeed, for the sake of brevity, conventional data networking, application development, and other functional aspects of the systems (and components of the individual operating components of the systems) may not be described in detail herein. Furthermore, the connecting lines shown in the various figures contained herein are intended to represent exemplary functional relationships and/or physical or virtual couplings between the various elements. It should be noted that many alternative or additional functional relationships or physical or virtual connections may be present in a practical electronic data communications system.

One skilled in the art will also appreciate that, for security reasons, any databases, systems, or components of the present invention may consist of any combination of databases or components at a single location or at multiple locations, wherein each database or system includes any of various suitable security features, such as firewalls, access codes, encryption, de-encryption, compression, decompression, and/or the like.

The scope of the invention should be determined by the appended claims and their legal equivalents, rather than by the examples given herein. For example, the steps recited in any method claims may be executed in any order and are not limited to the order presented in the claims. Moreover, no element is essential to the practice of the invention unless specifically described herein as "critical" or "essential."

As a computer processing device, any suitable device for performing computations in accordance with a computer program may be used. Examples of such devices include a personal computer, a laptop computer, a microprocessor, a programmable logic device, or an application specific integrated circuit.

While this invention has been described by reference to a preferred embodiment, it should be understood that numerous changes could be made within the spirit and scope of the inventive concepts described. Accordingly, it is intended that the invention not be limited to the disclosed embodiment, but that it have the full scope permitted by the language of the following claims.

What is claimed is:

1. A method of performing real-time defect recognition on a train wheel, comprising: detecting the train wheel entering a test station; accelerating a test head to match the speed of the train wheel; injecting, from the test head, pulses of a plurality of ultrasonic beams into the train wheel; detecting acoustic responses caused at a discontinuity of an elongated material; determining at least one characteristic of the detected acoustic responses; and determining a pattern of a feature of the wheel associated with said discontinuity based on the at least one characteristic and at least one pattern recognition rule.

2. The method of claim 1, wherein said at least one characteristic comprises a beam pulse speed.

3. The method of claim 1, wherein said step of determining the pattern comprises:
classifying features associated with the responses; clustering the classified features;
performing basic recognition analysis using the clustered classified features to determine a basic recognition; and
performing context recognition analysis on the basic recognition to determine the pattern.

4. A system for performing real-time defect detection on a train wheel, comprising:
a flange bearing track for the train wheel to ride on; a defect detection unit, said defect detection unit having at least one test head adapted to emit an ultrasonic beam and at least one ultrasonic detector; a test track adapted to carry the defect detection unit; a motor coupled to the defect detection unit transducer to move the defect detection unit on the test track; and a speed matching unit to match the speed of the defect detection unit with the train wheel under test.

5. The system of claim 4, wherein the motor is adapted to move the defect detection unit at about 3 to 10 miles per hour.

6. The system of claim 4, further comprising: a pattern recognition device coupled to the defect detection unit to optically detect surface defects.

7. A system for performing real-time defect detection on a railroad wheel, said system comprising: a test device being adapted to move along side a train wheel, said test device injecting pulses of a plurality of ultrasonic beams into the wheel and detecting acoustic responses caused at a discontinuity in the wheel; and a processor, said processor being programmed to determine a pattern of a feature of the wheel associated with said discontinuity at defect condition.

8. A system being capable of performing real-time defect detection and recognition on all train wheels in a train formation comprising: a plurality of test stations, each test station having a test head, adapted to detect and sequentially test all said train wheels; accelerating means to accelerate each individual test head to match the speed of a designated train wheel; injecting means and detecting means at each test head adapted to inject and detect acoustic responses caused at a discontinuity of an elongated material;
and determining at least one characteristic of the detected acoustic responses; and a processor, said processor coupled to each test head, said processor being programmed to determine a pattern of a feature of the wheel associated with a defect condition.

9. A remote, non-contact system for detecting a defect in a railroad wheel, said system comprising: a test unit, located at a first location parallel to the direction of travel of the railroad wheel and adapted to travel in synchronicity with the railroad wheel, for generating in a non-contact manner in said wheel an ultrasonic wave having a specified wavefront; and a detector, located at a second location parallel to the direction of travel of the railroad wheel adapted to travel in synchronicity with the railroad wheel, for sensing from said wheel the acoustic signal emanating from said wheel that results from said ultrasonic wave traveling through said wheel; signal processor, responsive to said sensed acoustic signal, capable of distinguishing whether said sensed signal has a component that indicates the existence of a defect in said railroad wheel.

* * * * *